US00PP35849P3

(12) United States Plant Patent
Olesen

(10) Patent No.: US PP35,849 P3
(45) Date of Patent: Jun. 4, 2024

(54) MINIATURE ROSE PLANT NAMED 'Poulty030'

(50) Latin Name: *Rosa hybrida*
Varietal Denomination: Poulty030

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,495

(22) Filed: Sep. 8, 2023

(65) Prior Publication Data

US 2024/0107909 P1 Mar. 28, 2024

(30) Foreign Application Priority Data

Sep. 30, 2022 (QZ) ..... PBR 2022/2174

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./101, 116
See application file for complete search history.

*Primary Examiner* — Susan McCormick Ewoldt

(57) ABSTRACT

A new garden rose plant of the Miniature class which has abundant, red flowers with a white stripe and attractive foliage. This new and distinct variety has shown to be uniform and stable in the resulting generations from asexual propagation.

1 Drawing Sheet

Botanical designation: *Rosa hybrida.*
Variety denomination: 'Poulty030'.

This application claims priority to Plant Breeder's Rights Application Number 2022/2174, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulty030', originated as a single seedling from the stated cross.

The new variety may be distinguished from its male pollen parent and female seed parent primarily by the following characteristics. The male pollen parent plant has red flowers while the new variety has red flowers with a white stripe. The female seed parent plant has pink and white stripe flowers while the new variety has red flowers with a white stripe. The female seed parent variety grows to a height of 65 cm while 'Poulty030' grows to a height of 38 cm.

The objective of the hybridization of this rose variety was to create a new and distinct variety with unique qualities, such as:

1. Uniform and abundant red flowers with a white stripe;
2. Vigorous, but very compact growth when propagated on its own roots;
3. Exceptional disease resistance.

This combination of qualities is not present in previously available commercial cultivars of this type, known to the inventor, and distinguish 'Poulty030' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulty030' was selected in the spring of 2016 by the inventor as a single plant from the progeny of the aforementioned hybridization.

Asexual reproduction of 'Poulty030' by rooted cuttings was first done by Mogens N. Olesen in the nursery in Fredensborg, Denmark in July, 2016. This initial and other subsequent asexual propagations conducted in controlled environments have demonstrated that the characteristics of 'Poulty030' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty030'.

Specifically illustrated in the drawing is a cluster of flowers on a branch, flower petals detached, flower buds upon opening, reproductive flower parts, open flowers viewed from above, juvenile leaves, mature leaves, and a bare stem. Plants shown are 4 months old.

DETAILED DESCRIPTION OF THE VARIETY

The following is a description of 'Poulty030', as observed in its growth in an indoor glasshouse nursery in Odense Denmark. Observed plants are 4 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulty019', U.S. Plant Pat. No. 26,051 are compared to the claimed plant. The claimed plant has a flower diameter of 52 mm while 'Poulty019' has a flower diameter of 40 mm. While the upper surface of the outer flower petals upon opening for 'Poulty030' is Red Group 53B with stripes of White Group N155B, the same feature for 'Poulty019' is Red Group 46A splashed with White Group N155B. In terms of flower fragrance, the comparison variety has a light floral scent, while the new plant has more fragrance described as a spicy, pine like perfume. The comparison variety tends to produce flowers singly while the new plant produces 15 to 20 flower buds per flowering stem.

FLOWER AND FLOWER BUD

Blooming habit: Continuous.

Flower bud:

- *Size.*—Upon opening, 20 mm in length from base of receptacle to end of bud. Bud diameter is 10 mm.
- *Bud form.*—Ovoid.
- *Bud color.*—As sepals divide petals are Red Group 53C.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have light to no foliaceous appendages on three of the five sepals.
- *Sepal size.*—About 30 mm long, 6 mm wide.
- *Receptacle.*—Texture: Smooth. Size: 4 mm in height, 5 mm wide. Color: Yellow-Green Group 144A. Shape: Campanulate.
- *Pedicel.*—Surface: Smooth. Length: 35 mm. Diameter: 2 mm on average. Color: Yellow-Green Group 144A. Strength: Strong.
- *Peduncle.*—Length: 15 to 20 mm. Diameter: About 3 mm. Color: Yellow-Green Group 144A. Texture: Smooth.

Flower bud development: Flower buds are borne in clusters of about 15 to 20 flower buds per stem.

Flower bloom:

- *Fragrance.*—Moderate spicy, pine like perfume.
- *Duration.*—The blooms have a duration on the plant of approximately 21 days. Petals fall cleanly away from plant after flowers have fully matured.
- *Size.*—Flower diameter is 52 mm when open. Flower depth is 15 mm.
- *Flower shape.*—Open cup, semi-double flower, with petals that curve out from the center.
- *Shape of flower, side view.*—The upper portion is flat convex, while the lower portion is flat.

Petalage: Under normal conditions, flowers have about 25 petals.

General tonality of flower: Open flowers are Red Group 53B to Red-Purple Group N57A with White Group N155B streaks.

Petal color:

- *Upon opening, outer and inner petals.*—Upper surface: Red Group 53B. Stripes White Group N155B. Lower surface: Red Group 53C with stripes of White Group N155B.
- *Basal petal spots.*—Upon opening no distinctive coloration.
- *After opening, outer and inner petals.*—Upper surface: Red-Purple Group N57B with stripes White Group N155B. Lower surface: Red-Purple Group N57B. Stripes White Group N155B.

Petals:

- *Petal reflex.*—Partially reflexed.
- *Margin.*—Entire and uniform with light undulations.
- *Shape.*—Broad and elliptic. Apex shape: Rounded. Base shape: Acute or obtuse.
- *Size.*—20 mm (l)×19 mm (w).
- *Texture.*—Smooth.
- *Thickness.*—Average.

Petaloids:

- *Size.*—10 mm (l) by 6 mm (w).
- *Quantity.*—About 3.
- *Shape.*—Elliptical with an acute base and acute apex.
- *Color.*—Red Group 53B on the upper surface, and Red Group 53C on the lower surface.

Reproductive flower parts:

- *Pollen.*—None observed.
- *Anthers.*—Size: 1 mm in length. Color: Greyed-Yellow Group 160D. Quantity: 35 on average.
- *Filaments.*—Color: Yellow Group 6D with light intonations of Orange-Red Group 35B. Length: 5 mm.
- *Pistils.*—Length: 4 mm. Quantity: 18 on average.
- *Stigmas.*—Color: Orange White Group 159D.
- *Styles.*—Color: Orange White Group 159D.
- *Location of stigmas.*—Level in location relative to the length of the filaments and the height of the anthers.
- *Hips.*—None Observed.

PLANT

Plant growth: Upright and bushy. Plants are about 38 cm in height, and 40 cm wide.

Stems:

- *Color of juvenile growth.*—Yellow-Green Group 144B.
- *Color of mature growth.*—Yellow-Green Group 144A.
- *Length.*—Canes are about 15 cm from the base of the plant to the flowering portion.
- *Diameter.*—About 4 mm.
- *Internodes.*—On mature canes about 32 mm between nodes.
- *Surface texture.*—Young wood: Smooth. Older wood: Smooth.

Long prickles:

- *Incidence.*—2 or 3 prickles per 10 cm of stem.
- *Size.*—Average length of prickles on mature stems is 4 mm.
- *Shape.*—Upper portion is linear. Lower portion is concave.
- *Color.*—Juvenile prickles: Greyed-Red Group 180D. Mature prickles: Greyed-Red Group 180D.

Plant foliage:

- *Compound leaf.*—About 78 mm (l)×45 (w).
- *Quantity.*—2 or 3 leaves per 10 cm of stem on average.
- *Leaf bearing angle to the stem.*—45 degrees.

*Color of juvenile foliage*.—Upper side: Yellow-Green Group 144A with intonations of Greyed-Red Group 181A. Lower side: Yellow-Green Group 144B.

*Color of mature foliage*.—Upper side: Yellow-Green Group 147A. Lower side: Yellow-Green Group 146A.

Plant leaves and leaflets:

*Stipules*.—Size: 14 mm long, 2 mm wide. Quantity: 2 per compound leaf. Shape: Linear, slightly broad based with outward extending apex. Margins: Finely serrated. Color: Yellow-Green Group 146A.

*Petiole*.—Length: On average 27 mm. Diameter: 2 mm. Upper surface color: Yellow-Green Group 144A. Lower surface color: Yellow-Green Group 144A.

*Rachis*.—Length: About 36 mm. Upper surface color: Yellow-Green Group 144A. Lower surface color: Yellow-Green Group 144A.

*Leaflet*.—Quantity: Normally 5 to 7 leaflets. Margins: Serrated. Size: Terminal leaflets are about 35 mm long, 25 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty030' substantially as described and illustrated herein.

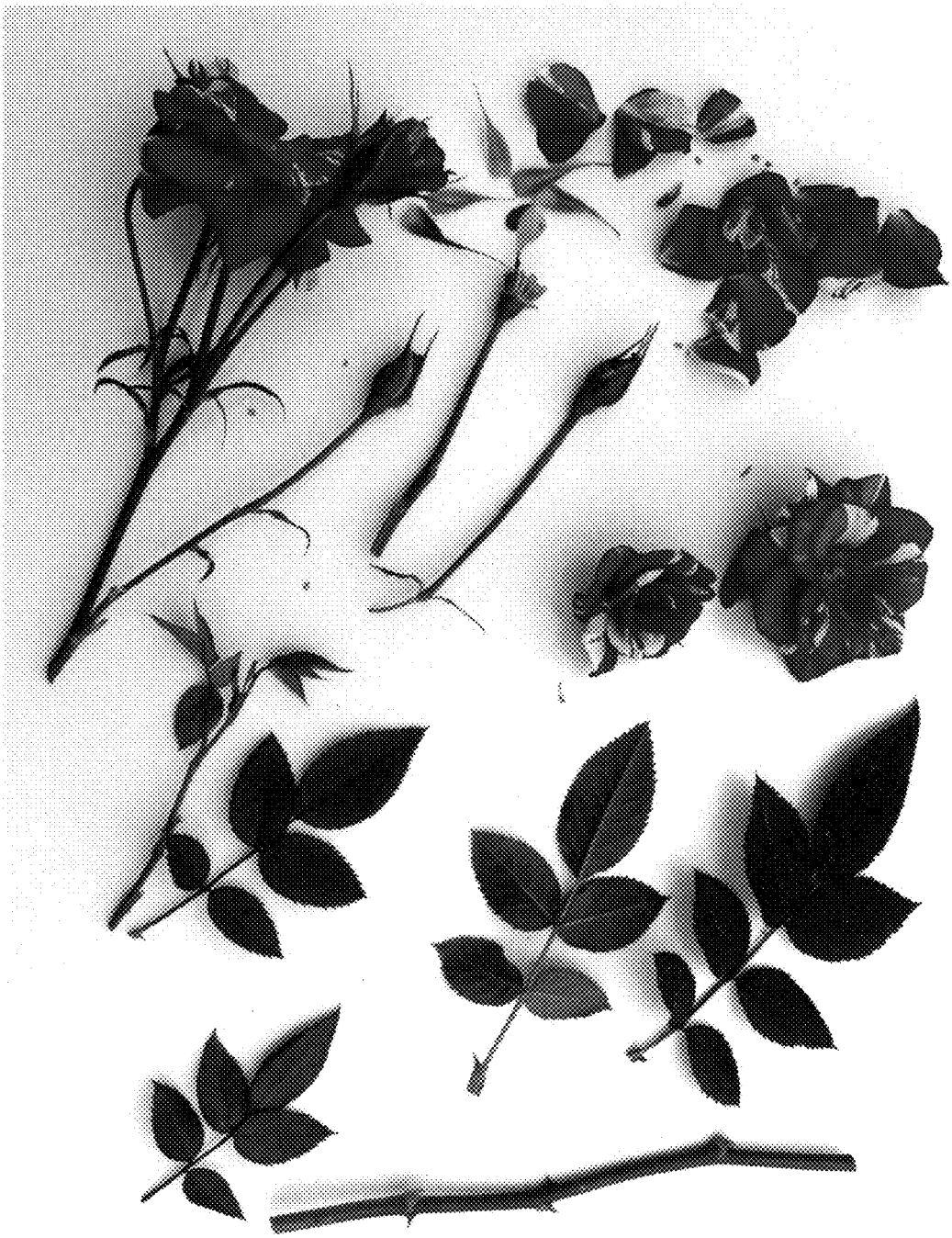

* * * * *